(12) United States Patent
Nielsen et al.

(10) Patent No.: US 6,432,288 B1
(45) Date of Patent: Aug. 13, 2002

(54) OXYGEN MONITOR

(76) Inventors: Ken E. Nielsen, 512 SE. $32^{nd}$ St., Ft. Lauderdale, FL (US) 33316; Poul K. Sorensen, Golvej 7, 9440 Abybro (DK)

( * ) Notice: Subject to any disclaimer, the term of this patent is extended or adjusted under 35 U.S.C. 154(b) by 0 days.

(21) Appl. No.: 09/829,180

(22) Filed: Apr. 10, 2001

(51) Int. Cl.$^7$ .......................... G01N 27/407; G01N 1/22
(52) U.S. Cl. .................. 204/424; 204/409; 73/863.51; 73/863.81; 73/864.33
(58) Field of Search ................................ 204/409, 424, 204/425, 426, 427, 428, 429; 73/863.81, 864.33, 863.83, 863.51, 864.81

(56) References Cited

U.S. PATENT DOCUMENTS

| | | |
|---|---|---|
| 4,040,930 A | 8/1977 | Dillon |
| 4,336,721 A * | 6/1982 | Curtis ......................... 204/409 |
| 4,339,318 A * | 7/1982 | Tanaka et al. .............. 204/408 |
| 4,875,990 A * | 10/1989 | Kodachi et al. ............ 204/408 |
| 5,241,853 A | 9/1993 | Tsuei et al. |
| 5,316,647 A | 5/1994 | Martell et al. |
| 5,496,450 A * | 3/1996 | Blumenthal et al. ........ 110/185 |
| 5,795,454 A | 8/1998 | Friese et al. |
| 5,846,391 A | 12/1998 | Friese et al. |
| 6,051,123 A * | 4/2000 | Joshi et al. ................. 204/412 |

OTHER PUBLICATIONS

"Toxic Gas CiTiceLs". City Technology product catalog.*

* cited by examiner

Primary Examiner—Robert J. Warden, Sr.
Assistant Examiner—Kaj K. Olsen
(74) Attorney, Agent, or Firm—Paul S. Rooy

(57) ABSTRACT

An oxygen monitor for a smokestack installation. The oxygen monitor includes a probe assembly mounted to the smokestack, a sensing assembly mounted to the probe assembly, and a monitor cabinet electrically connected to the sensing assembly. The probe assembly has an intake tube within an exhaust tube. Because the intake tube mouth is smaller than the effective exhaust tube mouth, the pressure reduction effect due to fluid travelling past the exhaust tube is greater than at the intake tube mouth, so fluid such as exhaust gasses tends to be drawn into the intake tube and towards an oxygen sensor. The fluid travels past the oxygen sensor and exits the probe assembly through the exhaust tube and its exhaust tube mouth, back into the smokestack. In addition, the hot oxygen sensor heats the fluid, causing it to rise into the exhaust tube and exit through its mouth. These two effects cause a self-circulation of the fluid being monitored for oxygen content, and eliminate the need for a separate fluid pump. The sensing assembly includes an oxygen sensor electrically connected to a transmitter. The transmitter is contained in a transmitter housing which is electrically insulated from the oxygen sensor. In addition, the transmitter is contained in a transmitter housing, and the transmitter is electrically insulated from the transmitter housing.

18 Claims, 4 Drawing Sheets

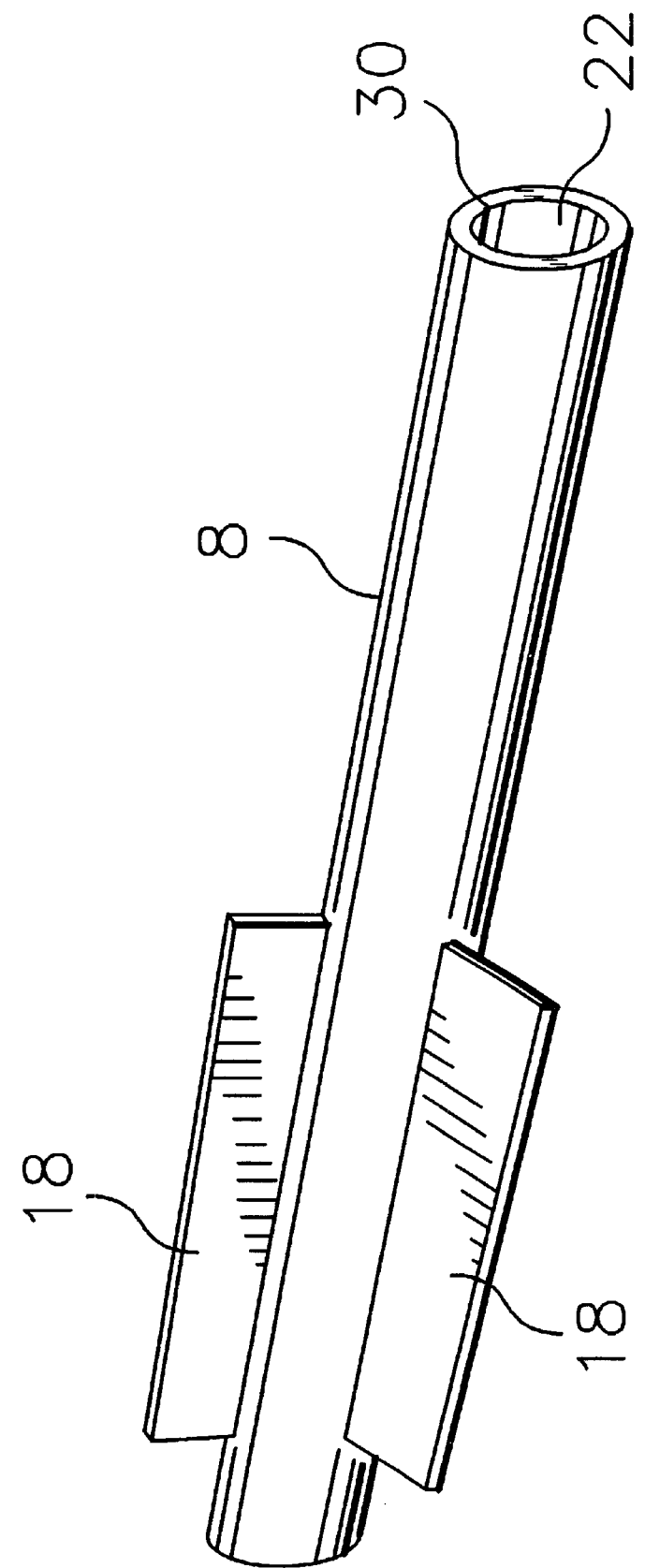

OXYGEN MONITOR

BACKGROUND OF THE INVENTION

1. Field of the Invention

This invention relates to gas measurement devices, and in particular to an oxygen monitor.

2. Background of the Invention

Ships are used extensively all over the world in order to transport combustible fluids in their tanks. The types of combustible fluid carried may include crude oil, refined fuel oil, etc. In order to reduce the chances of a fire occurring, oxygen present in the tanks must be pumped out before the tanks are filled with a combustible fluid. For example, in the case of crude oil, oxygen must be pumped out of the tanks until less than 8% oxygen content remains in the tank.

Normally, exhaust gasses from the ship's main burners are used to displace oxygen-rich air from combustible fluid tanks. The exhaust gasses used for this purpose should contain less than 5% oxygen. The oxygen content of the exhaust gasses used to evacuate the ship's tanks is monitored by means of oxygen monitors mounted on the ship's smokestack(s). Before combustible fluids are pumped into the ship's tanks, hand-held oxygen monitors are employed in the tanks themselves to make sure that the maximum safe oxygen percentage is not exceeded.

Existing Designs

Existing smokestack-mounted oxygen monitors typically use a vacuum pump to extract smoke samples from the smokestack, and the exhaust gasses are then pumped to a location where the monitor itself is located. There are a number of disadvantages associated with this scheme.

A first disadvantage involves calibration. this type of setup requires calibration of the. oxygen monitor every month or so. The calibration operation itself is a multi-step process which is time-consuming and expensive. Typically two calibration percentages are used (e.g. 4% and 16%); a calibration curve is fitted to these two points, then the two calibration points are re-checked to ensure accuracy. The entire process takes approximately ½–1 hour of time. When the calibration process is multiplied by several monitors, and several smokestacks, over many months of operation, the time waste is considerable.

A second disadvantage involves the physical placement of the oxygen monitor. Because smoke is physically pumped from the smokestack to the location where the oxygen monitor is located, the distance from smokestack to. monitor is limited. Thus, it can be difficult to locate the monitor in a convenient place.

SUMMARY OF THE INVENTION

Accordingly, it is an object of the present invention to provide an oxygen monitor which does not require frequent calibration. Design features allowing this object to be accomplished include the use of a zirconium dioxide oxygen sensor. Advantages associated with the accomplishment of this object include the elimination of monthly monitor inspections, along with the associated cost saving,s.

It is another object of the present invention to provide an oxygen monitor whose monitor cabinet may be located remote from the smokestack. Design features allowing this object to be accomplished include a sensing assembly electrically connected to a remotely located monitor cabinet. Benefits associated with the accomplishment of this object include more convenient location of the monitor cabinet, along with the associated reduced time to view and/or maintain the monitor cabinet, and consequent cost savings.

It is another object of the present invention to provide an oxygen monitor which requires no suction pump to bring exhaust gasses from the smokestack to the oxygen sensor. Design features allowing this object to be accomplished include an intake tube mounted within an exhaust tube, a pressure differential caused by exhaust gas flow between an intake tube mouth and an exhaust tube mouth, and a heated oxygen sensor. Benefits associated with the accomplishment of this object include simpler design with less required components, and hence reduced necessity of maintenance, and decreased costs.

BRIEF DESCRIPTION OF THE DRAWINGS

The invention, together with the other objects, features, aspects and advantages thereof will be more clearly understood from the following in conjunction with the accompanying drawings.

Four sheets of drawings are provided. Sheet one contains FIG. 1. Sheet two contains FIG. 2. Sheet three contains FIG. 3. Sheet four contains FIG. 4.

FIG. 4 is a side isometric view of an intake tube.

DETAILED DESCRIPTION OF THE PREFERRED EMBODIMENT

Figure 1:
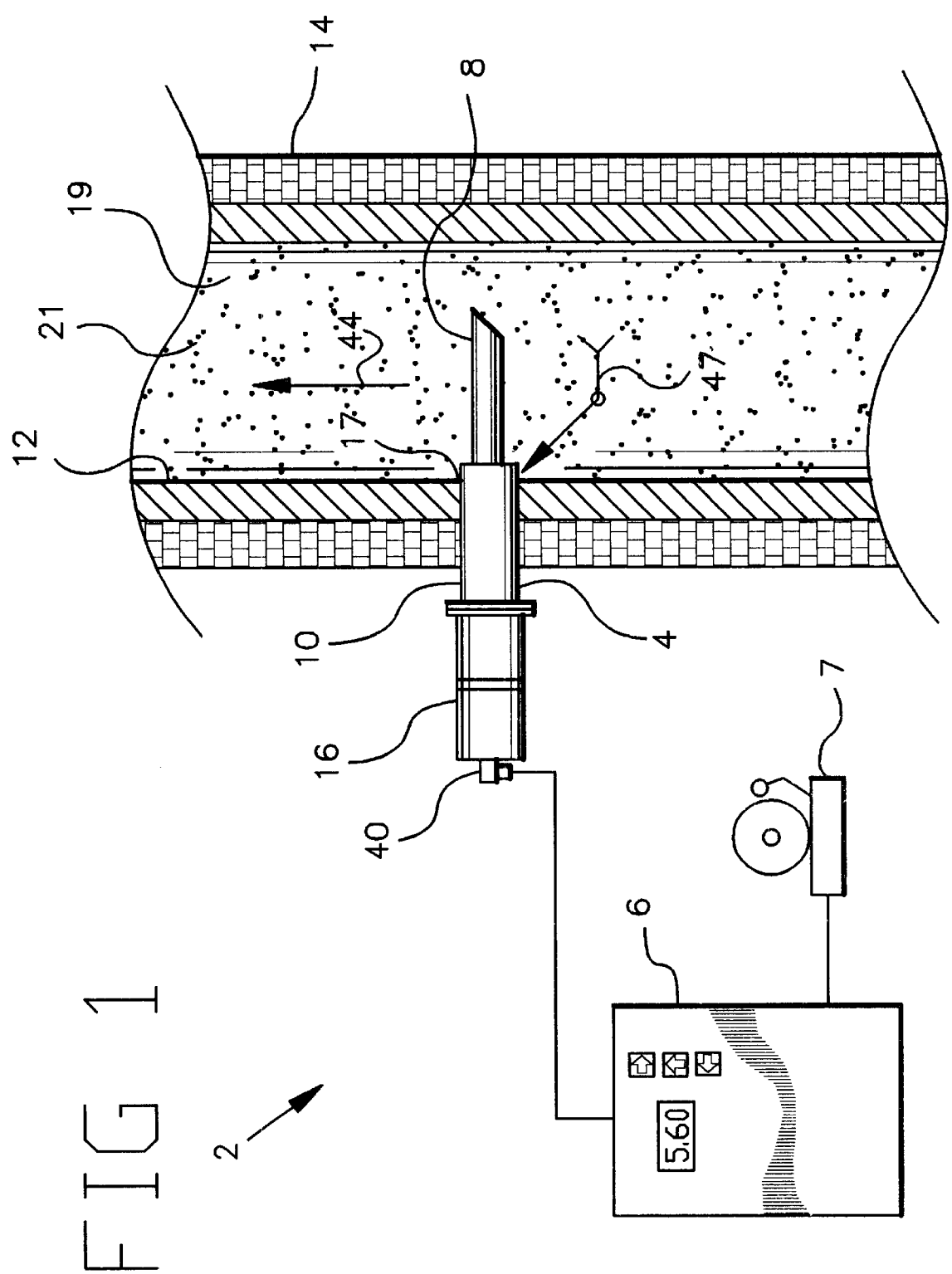
FIG. 1 is a side schematic view of an oxygen monitor.

FIG. 1 is a side schematic view of oxygen monitor 2. Oxygen monitor 2 comprises sensing assembly 16 physically and electrically attached to probe assembly 4, and monitor cabinet 6 electrically connected to sensing assembly 16. Probe assembly 4 is mounted to smokestack 12 through insulation 14 and smokestack aperture 17. One method to attach probe assembly 4 to smokestack 12 is by welding, as indicated by weld symbol 47.

Figure 2:
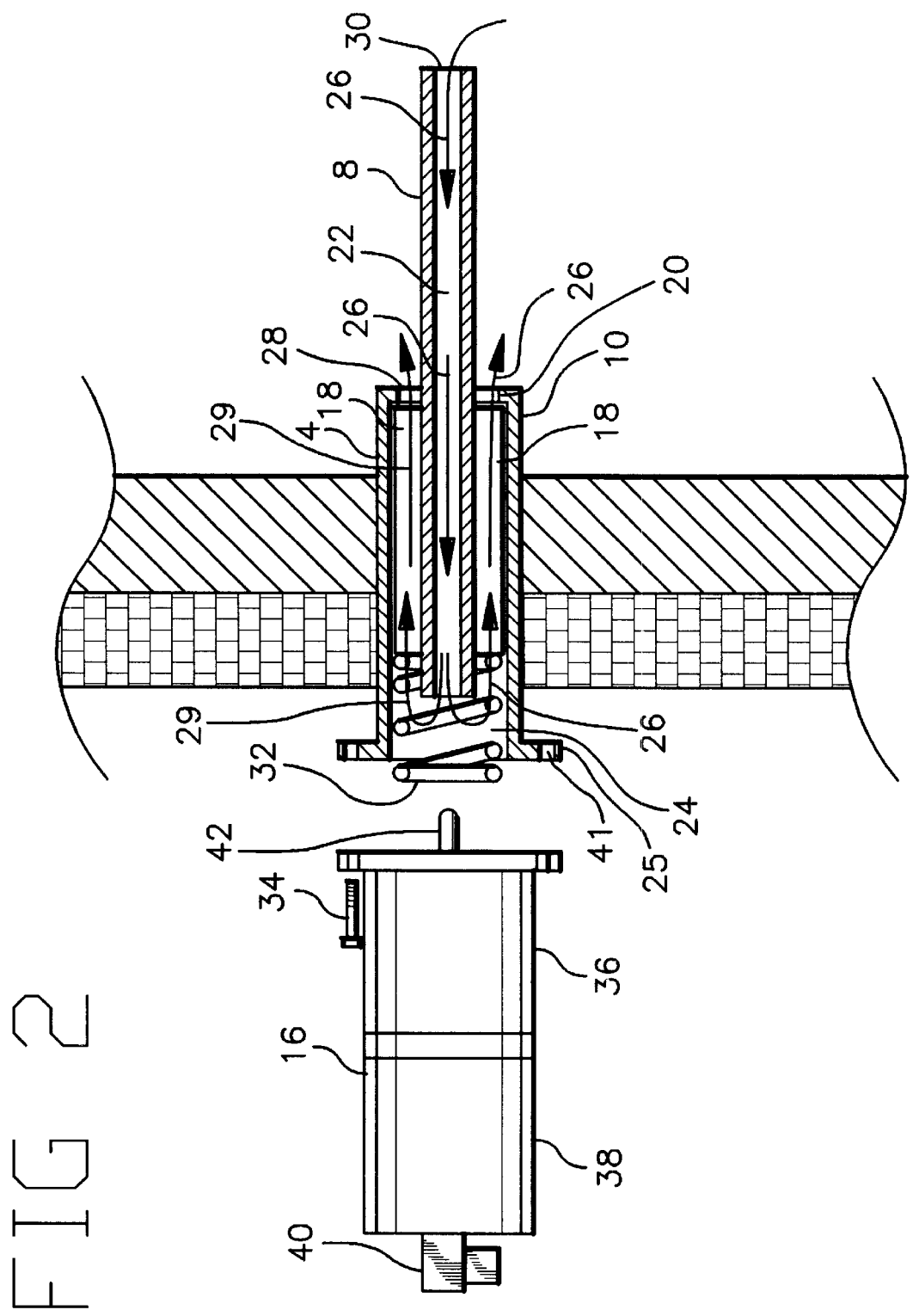
FIG. 2 is a side cross-sectional exploded view of a sensing assembly and a probe assembly, the probe assembly being mounted on a smokestack.
Figure 3:
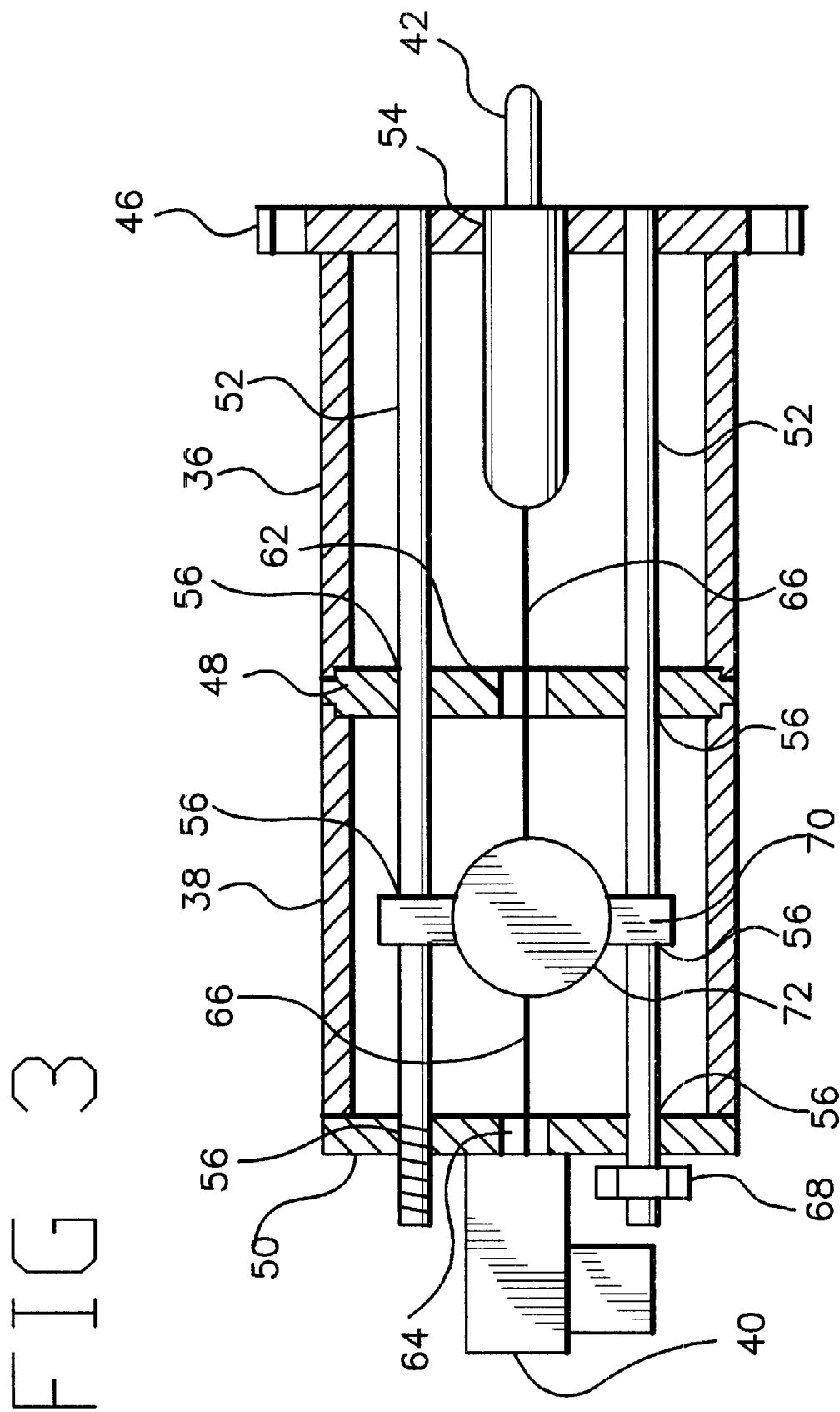
FIG. 3 is a side cross-sectional view of a sensing assembly.

Smokestack 12 contains exhaust gasses 19 travelling through smokestack bore 21 as indicated by arrow 44. In operation, oxygen monitor 2 samples the oxygen content of exhaust gasses 19 by drawing exhaust gasses 19 into probe assembly 4 through intake tube 8. Referring now also to FIGS. 2, 3 and 4, oxygen sensor 42 mounted in sensing assembly 16 then measures the oxygen content of exhaust gasses 19, renders the oxygen concentration directly proportional to a voltage signal, and transmits same to monitor cabinet 6.

Alarm cabinet 6 visually displays the oxygen concentration, and alarm 7 may be electrically attached to monitor cabinet 6 and set to sound when the oxygen concentration reaches a pre-determined threshold value. As depicted in FIG. 1, monitor cabinet 6 may be electrically attached to sensing assembly 16 by means of wire 66 and multiconnector jack 40.

FIG. 2 is a side cross-sectional exploded view of sensing assembly 16 and probe assembly 4, probe assembly 4 being mounted to smokestack 12. Probe assembly 4 comprises intake tube 8 slidably engaged with exhaust tube 10, and springy 32. As may be more clearly observed in FIG. 4, intake tube 8 comprises axially-disposed intake tube bore 22, intake tube mouth 30 at one extreme, and at least one intake tube fin 18 mounted on the outside of intake tube 8 at an extreme of intake tube 8 opposite intake tube mouth 30.

Exhaust tube 10 comprises axially-disposed exhaust tube bore 24, exhaust tube mouth 28 at one extreme, and exhaust tube flange 25 at an extreme of exhaust tube 10 opposite exhaust tube mouth 28. Exhaust tube flange 25 comprises at least one bolt hole 41 sized to admit bolt 34. Exhaust tube lip 20 is disposed around exhaust tube mouth 28, and serves to constrain intake tube fin(s) 18 (and consequently also the extreme of intake tube 8 to which exhaust fin(s) 18 are attached) within exhaust tube 10.

Referring now to FIG. 3, sensing assembly 16 comprises sensor housing 36 attached to transmitter housing 38. Sensor housing 36 is separated from transmitter housing 38 by means of interhousing bulkhead 48. Interhousing bulkhead 48 is made of electrically non-conducting material, and thus serves to electrically insulate sensor housing 36 from transmitter housing 38. Sensor bulkhead 46 is disposed at an extreme of sensor housing 36 opposite interhousing bulkhead 48. Sensor bulkhead 46 comprises at least one bolt hole 41 sized to slidably admit bolt 34. In the preferred embodiment, during installation of oxygen sensor 2 sensing assembly 16 is mounted to probe assembly 4 by means of bolt(s) 34. Sensor bulkhead 46 also comprises sensor aperture 54 sized to admit oxygen sensor 42.

Jack bulkhead 50 is attached to an extreme of transmitter housing 38 opposite interhousing bulkhead 48. Multiconnector jack 40 is attached to jack bulkhead 50. Thus, sensing assembly 16 comprises transmitter housing 38 sandwiched between jack bulkhead 50 and interhousing bulkhead 48, and sensor housing 36 sandwiched between interhousing bulkhead 48 and sensor bulkhead 46. At least one threaded rod 52 is rigidly attached to sensor bulkhead 46. Jack bulkhead 50 and interhousing bulkhead 48 each comprise one rod bore 56 corresponding to each rod 52 attached to sensor bulkhead 46. When sensing assembly 16 is assembled, threaded rod(s) 52 rigidly attached to sensor bulkhead 46 and passing through rod bores 56, in combination with nut(s) 68 sized to mate with threaded rod(s) 52, hold sensing assembly 16 together.

Transmitter 72 is disposed within transmitter housing 38, and is mounted to transmitter bridge 70. Transmitter bridge comprises at least one rod bore 56 sized to frictionally admit a threaded rod 52. Thus, transmitter 72 is mounted to transmitter bridge 70, which in turn is mounted to at least one threaded rod 52. In the preferred embodiment, transmitter bridge 70 was made of electrically non-conducting material, thus electrically insulating transmitter 72 from threaded rod(s) 52.

Interhousing bulkhead 48 and jack bulkhead 50 comprise interhousing bulkhead aperture 62. and jack bulkhead aperture 64 respectively. Oxygen sensor 42 is electrically connected to transmitter 72 by means of wire 66 passing through interhousing bulkhead aperture 62. Transmitter 72 is electrically connected to multi-connector jack 40 by means of wire 66 passing through jack bulkhead aperture 64.

In the preferred embodiment, oxygen sensor 42 was a zirconium oxygen. sensor. Zirconium oxygen sensors are well-known in the art, and incorporate zirconium dioxide in their construction. They operate on the comparative principle, where atmospheric air is used as reference air.

Atmospheric air has a known composition of approximately 21% oxygen. Exhaust gasses 19 are in contact with one side of the sensor, and atmospheric air with the other side . The sensor is heated by means of an electrical heating element to maintain it at a temperature of approximately 650° C. When the oxygen concentrations on the two sides differ, a migration of oxygen ions occurs, thus producing a low voltage signal which is logarithmically proportional to the difference in oxygen concentrations. This low voltage signal travels from oxygen sensor 42 to transmitter 72 through wire 66. Transmitter 72 amplifies the logarithmic signal and renders it linear in the operating range of 0.5%–21% oxygen level, and sends the amplified linear signal through wire 66 to monitor cabinet 6.

Because of the electrical wire connection between sensing assembly 16 and monitor cabinet 6, monitor cabinet 6 may be located wherever is most convenient for. the operator to observe its display, thus contributing both to time efficiency and safety. In. addition, alarm 7 may be electrically attached to monitor cabinet 6 and set to sound when the oxygen concentration reaches a pre-determined threshold value, thus alerting the operator to a possibly hazardous oxygen level.

When sensing assembly 16 is mounted to exhaust tube 10, spring 32 urges fin(s) 18 attached to intake tube 8 against exhaust tube lip 20, thus securely immobilizing intake tube 8 within smokestack bore 21. In operation, exhaust gasses flowing past exhaust tube mouth 28 as indicated by arrow 44 in FIG. I cause an area of lower pressure at exhaust tube mouth 28 and at intake tube mouth 30. Because the cross-sectional area of exhaust tube mouth 28 minus the cross-sectional area of intake tube 8 is greater than the cross-sectional area of intake tube mouth 30, the pressure reduction effect at exhaust tube mouth 28 is greater than that at intake tube mouth 30. This differential causes exhaust gasses to flow into intake tube mouth 30, through intake tube bore 22, past oxygen sensor 42, and thence through exhaust tube bore 24 and out through exhaust tube mouth 28 as indicated by arrows 26.

This self-circulation of exhaust gasses 19 is increased by the temperature of oxygen sensor 42, which has the effect of heating the exhaust gasses 19 brought to it as described above, which then tend to rise and escape through the upper portion of exhaust tube 10 as indicated by arrows 29. The self-circulation of exhaust gasses 19 scheme comprises an important part of the instant invention, because the need for a prior art suction pump is completely avoided.

As may be observed in FIG. 1, the end of intake tube 8 which extends into smokestack bore 21 may be cut off at an angle of approximately 45 degrees, with the resulting elliptical shape of intake tube mouth 30 facing downwards into the flow of exhaust gasses 19. This geometry has the effect of aiding the flow of exhaust gasses 19 into intake tube bore 22 and thence to oxygen sensor 42. Absent such 45 degree geometry, the pressure differential effect described above and/or the heating effect of oxygen sensor 42 provide the required circulation of exhaust gasses 19 past oxygen sensor 42.

In the preferred embodiment, intake tube 8, exhaust tube 10, spring 32, sensor bulkhead 46, sensor housing 36, transmitter housing 38 and rod(s) 52 were made of metal, synthetic, or other appropriate material. Interhousing bulkhead 48 and transmitter bridge 70 were made of an electrically insulating material such as Teflon, or other appropriate material. Oxygen sensor 42, multiconnector jack 40, wire 66, alarm 7 and the electronics components of monitor cabinet 6 were commercially available, off-the-shelf components.

While a preferred embodiment of the invention has been illustrated herein, it is to be understood that changes and variations may be made by those skilled in the art without departing from the spirit of the appending claims.

DRAWING ITEM INDEX 2 oxygen monitor
4 probe assembly
6 monitor cabinet
7 alarm
8 intake tube
10 exhaust tube
12 smokestack
14 insulation 16 sensing, assembly
17 smokestack aperture
18 intake tube fin
19 exhaust gasses
20 exhaust tube lip
21 smokestack bore
22 intake tube bore
24 exhaust tube bore
25 exhaust tube flange
26 arrow
27 threaded bore
28 exhaust tube mouth
29 arrow
30 intake tube mouth
32 spring
34 bolt
36 sensor housing
38 transmitter housing
40 multiconnector jack
41 bolt hole
42 oxygen sensor
44 arrow
46 sensor bulkhead
47 weld symbol
48 interhousing bulkhead
50 jack bulkhead
52 threaded rod
54 sensor aperture
56 rod bore
62 interhousing bulkhead aperture
64 jack bulkhead aperture
66 wire
68 nut
70 transmitter bridge
72 transmitter

We claim:

1. An oxygen monitor comprising a probe assembly and a monitor cabinet electrically connected to a sensing assembly, said probe assembly comprising an intake tube and an exhaust tube, said intake tube comprising an intake tube bore terminating at one extreme in an intake tube mouth, said exhaust tube comprising an exhaust tube bore terminating at one extreme in an exhaust tube mouth, an extreme of said intake tube opposite said intake tube mouth being disposed within said exhaust tube, an oxygen sensor extending from said sensing assembly into said probe assembly, and means of inducing circulation of a fluid into said intake tube mouth, through said intake bore, into said exhaust tube bore, and out through said exhaust tube mouth, both said intake tube mouth and said exhaust tube mouth being disposed within a fluid to be monitored, a cross-sectional shape of said exhaust tube mouth being an annulus whose inside diameter is defined by said intake tube.

2. The oxygen monitor of claim 1 wherein said means of inducing circulation comprises an intake tube mouth cross-sectional area which is less than an exhaust tube mouth cross-sectional area minus an intake tube cross-sectional area, whereby a pressure reduction effect at said intake tube mouth is greater than a pressure reduction effect at said intake tube mouth, thereby causing a circulation of flow into said intake tube mouth, through said intake tube bore, past said oxygen sensor, through said exhaust tube and out said exhaust tube mouth.

3. The oxygen monitor of claim 2 wherein an extreme of said intake probe opposite said sensing assembly terminates at substantially a 45 degree angle and said intake tube mouth faces into a fluid flow.

4. The oxygen monitor of claim 1 wherein said means of inducing circulation comprises a heated oxygen sensor, whereby passing fluid is heated, thereby causing said fluid to rise and exit said exhaust tube bore through said exhaust tube mouth.

5. The oxygen monitor of claim 1 wherein said sensing assembly comprises a sensor housing attached to a transmitter housing, means of insulating said sensor housing from said transmitter housing, a sensor bulkhead disposed at an extreme of said sensor housing opposite said transmitter housing, said oxygen sensor extending through said sensor bulkhead, a transmitter disposed within said transmitter housing, and means of electrically insulating said transmitter from said transmitter housing, said oxygen sensor being electrically connected to said transmitter, said transmitter being electrically connected to said monitoring cabinet.

6. The oxygen monitor of claim 5 wherein said means of insulating said sensor housing from said transmitter housing comprises an interhousing bulkhead between said sensor housing and said transmitter housing, said interhousing bulkhead being made of electrically non-conductive material.

7. An oxygen monitor comprising a probe assembly and a monitor cabinet electrically connected to a sensing assembly, said probe assembly comprising an intake tube and an exhaust tube, said intake tube comprising an intake tube bore terminating at one extreme in an intake tube mouth, said exhaust tube comprising an exhaust tube bore terminating at one extreme in an exhaust tube mouth, an extreme of said intake tube opposite said intake tube mouth being disposed within said exhaust tube, an oxygen sensor extending from said sensing assembly into said probe assembly, and means of inducing circulation of a fluid into said intake tube mouth, through said intake bore, into said exhaust tube bore, and out through said exhaust tube mouth comprising an intake tube mouth cross-sectional area which is less than an exhaust tube mouth cross-sectional area minus an intake tube cross-sectional area, said sensing assembly comprising a spring, said intake tube comprising at least one fin, and said exhaust tube comprising an exhaust tube lip, said spring urging said at least one intake tube fin against said exhaust tube lip, whereby said intake tube is immobilized.

8. An oxygen monitor comprising a probe assembly and a monitor cabinet electrically connected to a sensing assembly, said probe assembly comprising an intake tube and an exhaust tube, said intake tube comprising an intake tube bore terminating at one extreme in an intake tube mouth, said exhaust tube comprising an exhaust tube bore terminating at one extreme in an exhaust tube mouth, an extreme of said intake tube opposite said intake tube mouth being disposed within said exhaust tube, an oxygen sensor extending from said sensing assembly into said probe assembly, and means of inducing circulation of a fluid into said intake tube mouth, through said intake bore, into said exhaust tube bore, and out through said exhaust tube mouth, said sensing assembly comprising a sensor housing attached to a transmitter housing, means of insulating said sensor housing from said transmitter housing, a sensor bulkhead disposed at an extreme of said sensor housing opposite said transmitter housing, said oxygen sensor extending through said sensor bulkhead, a transmitter disposed within said transmitter housing, and means of electrically insulating said transmitter from said transmitter housing, said oxygen sensor being electrically connected to said transmitter, said transmitter being electrically connected to said monitoring cabinet, said means of electrically insulating said transmitter from said transmitter housing comprising a transmitter bridge made of electrically non-conductive material, said transmitter being mounted to said transmitter bridge.

9. An oxygen monitor comprising a probe assembly and a monitor cabinet electrically connected to a sensing assembly, said probe assembly comprising an intake tube and an exhaust tube, said intake tube comprising an intake tube bore terminating at one extreme in an intake tube mouth, said exhaust tube comprising an exhaust tube bore terminating at one extreme in an exhaust tube mouth, an extreme of said intake tube opposite said intake tube mouth being disposed within said exhaust tube, an oxygen sensor extending from said sensing assembly into said probe assembly, and means of inducing circulation of a fluid into said intake tube mouth, through said intake bore, into said exhaust tube bore, and out through said exhaust tube mouth, said sensing assembly comprising a sensor housing attached to a transmitter housing, means of insulating said sensor housing from said transmitter housing, a sensor bulkhead disposed at an extreme of said sensor housing opposite said transmitter housing, said oxygen sensor extending through said sensor bulkhead, a transmitter disposed within said transmitter housing, and means of electrically insulating said transmitter from said transmitter housing, said oxygen sensor being electrically connected to said transmitter, said transmitter being electrically connected to said monitoring cabinet, said means of insulating said sensor housing from said transmitter housing comprising an interhousing bulkhead between said sensor housing and said transmitter housing, said interhousing bulkhead being made of electrically non-conductive material, at least one threaded rod attached to said sensor bulkhead, a jack bulkhead disposed at an extreme of said transmitter housing opposite said sensor housing, a rod bore in said interhousing bulkhead corresponding to each said at least one threaded rod, a rod bore in said jack bulkhead corresponding to each said at least one threaded rod, and a nut corresponding to and sized to mate with said at least one threaded rod, each said at least one threaded rod being disposed through the corresponding rod bore in said interhousing bulkhead and the corresponding rod bore in said jack bulkhead.

10. The oxygen monitor of claim 9 wherein said means of electrically insulating said transmitter from said transmitter housing comprises a transmitter bridge made of electrically non-conductive material, said transmitter being mounted to said transmitter bridge, and a rod bore in said transmitter bridge corresponding to each said at least one threaded rod, one said threaded rod extending through each said transmitter bridge rod bore.

11. The oxygen monitor of claim 10 wherein said interhousing bulkhead comprises an interhousing bulkhead aperture and said jack bulkhead comprises a jack bulkhead aperture, said oxygen sensor being electrically connected to said transmitter by means of wire extending through said interhousing bulkhead aperture, and said transmitter being electrically connected to said monitoring cabinet by means of wire extending through said jack bulkhead aperture.

12. The oxygen monitor of claim 11 wherein said exhaust tube further comprises an exhaust tube flange disposed at an extreme, of said exhaust tube opposite said exhaust tube mouth, at least one bolt hole in said exhaust tube flange, at least one bolt hole in said sensor bulkhead, and at least one bolt sized to fit through said bolt holes, whereby said sensing assembly may be removably attached to said probe assembly.

13. An oxygen monitor comprising a probe assembly attached to a sensing assembly, said probe assembly comprising an intake tube and an exhaust tube, said intake tube comprising an intake tube bore terminating at one extreme in an intake tube mouth, said exhaust tube comprising an exhaust tube bore terminating at one extreme in an exhaust tube mouth, an extreme of said intake tube opposite said intake tube mouth being disposed within said exhaust tube, an oxygen sensor extending from said sensing assembly into said probe assembly, and means of inducing circulation of a fluid into said intake tube mouth, through said intake bore, into said exhaust tube bore, and out through said exhaust tube mouth, both said intake tube mouth and said exhaust tube mouth being disposed within a fluid to be monitored, a cross-sectional shape of said exhaust tube mouth being an annulus whose inside diameter is defined by said intake tube.

14. The oxygen monitor of claim 13 wherein said means of inducing circulation comprises an intake tube mouth cross-sectional area which is less than an exhaust tube mouth cross-sectional area minus an intake tube cross-sectional area, whereby a pressure reduction effect at said intake tube mouth is greater than a pressure reduction effect at said intake tube mouth, thereby causing a circulation of flow into said intake tube mouth, through said intake tube bore, past said oxygen sensor, through said exhaust tube and out said exhaust tube mouth.

15. The oxygen monitor of claim 14 wherein an extreme, of said intake probe opposite said sensing assembly terminates at substantially a 45 degree angle, and said intake tube mouth faces into a fluid flow.

16. The oxygen monitor of claim 13 wherein said means of inducing circulation comprises a heated oxygen sensor, whereby passing fluid is heated, thereby causing said fluid to rise and exit said exhaust tube bore through said exhaust tube mouth.

17. The oxygen monitor of claim 13 wherein said sensing assembly comprises a sensor housing attached to a housing, means of insulating said sensor housing from said transmitter housing, a sensor bulkhead disposed at an extreme of said sensor housing opposite said transmitter housing, said oxygen sensor extending through said sensor bulkhead, a transmitter disposed within said transmitter housing, and means of electrically insulating said transmitter from said transmitter housing, said oxygen sensor being electrically connected to said transmitter, said transmiter being electrical connected to a monitoring cabinet.

18. An oxygen monitor comprising a probe assembly electrically connected to a sensing assembly, said probe assembly comprising an intake tube and an exhaust tube, said intake tube comprising an intake tube bore terminating at one extreme in an intake tube mouth, said exhaust tube comprising an exhaust tube bore terminating at one extreme in an exhaust tube mouth, an extreme of said intake tube opposite said intake tube mouth being disposed within said exhaust tube, an oxygen sensor extending from said sensing assembly into said probe assembly, and means of inducing circulation of a fluid into said intake tube mouth, through said intake bore, into said exhaust tube bore, and out through said exhaust tube mouth, said sensing assembly comprising a spring, said intake tube comprising at least one fin, and said exhaust tube comprising an exhaust tube lip, said spring urging said at least one intake tube fin against said exhaust tube lip, whereby said intake tube is mobilized.

* * * * *

UNITED STATES PATENT AND TRADEMARK OFFICE
CERTIFICATE OF CORRECTION

PATENT NO.    : 6,432,288 B1
DATED         : August 13, 2002
INVENTOR(S)   : Nielsen et al.

It is certified that error appears in the above-identified patent and that said Letters Patent is hereby corrected as shown below:

Column 1,
Line 33, is "calibration. this…" should be -- calibration: this… --
Line 34, is "the. oxygen…" should be -- the oxygen… --
Line 47, is "to. monitor…" should be -- to monitor… --
Line 58, is "…saving,s." should be -- …savings. --

Column 2,
Line 61, is "…springy 32." should be -- …spring 32. --

Column 3,
Line 46, is "…aperture 62. and…" should be -- …aperture 62 and… --
Line 52, is "…oxygen. sensor…" should be -- …oxygen sensor… --

Column 4,
Line 5, is "…for. the operator…" should be -- …for the operator… --

Column 5,
Line 1, is "16 sensing, assembly" should be -- 16 sensing assembly --

Column 7,
Line 59, is "…extreme, of said…" should be -- …extreme of said… --

Column 8,
Line 45, is "…being electrical connected…" should be -- …being electrically connected… --

Signed and Sealed this

Eleventh Day of February, 2003

JAMES E. ROGAN
*Director of the United States Patent and Trademark Office*